(12) United States Patent
Kohler et al.

(10) Patent No.: US 9,687,681 B2
(45) Date of Patent: Jun. 27, 2017

(54) THERAPY SYSTEM WITH TEMPERATURE CONTROL

(75) Inventors: Max Oskar Kohler, Espoo (FI); Shunmugavelu Sokka, Brighton, MA (US)

(73) Assignee: Koninklijke Philips N.V., Eindhoven (NL)

( * ) Notice: Subject to any disclaimer, the term of this patent is extended or adjusted under 35 U.S.C. 154(b) by 358 days.

(21) Appl. No.: 12/812,240

(22) PCT Filed: Jan. 9, 2009

(86) PCT No.: PCT/IB2009/050080
§ 371 (c)(1),
(2), (4) Date: Jul. 9, 2010

(87) PCT Pub. No.: WO2009/090579
PCT Pub. Date: Jul. 23, 2009

(65) Prior Publication Data
US 2010/0280356 A1    Nov. 4, 2010

Related U.S. Application Data

(60) Provisional application No. 61/020,782, filed on Jan. 14, 2008.

(51) Int. Cl.
*A61N 7/02* (2006.01)
*A61B 5/01* (2006.01)
(Continued)

(52) U.S. Cl.
CPC ............... *A61N 7/02* (2013.01); *A61B 5/015* (2013.01); *A61B 5/055* (2013.01); *A61B 2017/00084* (2013.01); *A61B 2090/374* (2016.02)

(58) Field of Classification Search
CPC .... A61N 7/02; A61B 2090/374; A61B 5/015; A61B 5/055; A61B 2017/00084
See application file for complete search history.

(56) References Cited

U.S. PATENT DOCUMENTS 5,485,839 A * 1/1996 Aida et al. .................... 600/427
5,590,653 A * 1/1997 Aida et al. .................... 600/411
(Continued)

FOREIGN PATENT DOCUMENTS

EP        1110508       6/2001
JP        H11226046 A   8/1999
(Continued)

OTHER PUBLICATIONS

D. Arora, et al., "Nonlinear Model Predictive Thermal Dose Control of Thermal Therapies: Experimental Validation With Phantoms", Proceeding of the 2004 American Control Conference, Boston, MA, Jul. 30, 2004, pp. 1627-1632.
(Continued)

*Primary Examiner* — Long V Le
*Assistant Examiner* — Angela M Hoffa

(57) ABSTRACT

A therapy system comprises a therapy module to direct a therapeutic action to a target along successive trajectories in a target zone that includes the target. A thermometry module is provided to measure temperature in a measurement field and to compute a thermal dose. The measurement field at least partially covers the target zone. A control module controls the therapy module to switch the therapeutic action to a next successive trajectory on the basis of the measured temperature or thermal dose. The successive trajectories are located inside of or outside of one another within the target zone. The therapeutic action comprises application of a focused ultrasound beam to the target. Temperature measurement is done on the basis of magnetic resonance signals.

9 Claims, 2 Drawing Sheets

(51) Int. Cl.
  *A61B 5/055* (2006.01)
  *A61B 17/00* (2006.01)
  *A61B 90/00* (2016.01)

(56) References Cited

U.S. PATENT DOCUMENTS

| | | | |
|---|---|---|---|
| 5,779,696 A | | 7/1998 | Berry et al. |
| 5,938,600 A | * | 8/1999 | Van Vaals et al. ............ 600/411 |
| 6,050,943 A | * | 4/2000 | Slayton et al. ............... 600/439 |
| 6,088,613 A | * | 7/2000 | Unger ........................... 600/420 |
| 6,128,522 A | | 10/2000 | Acker et al. |
| 6,374,132 B1 | | 4/2002 | Acker et al. |
| 6,418,337 B1 | * | 7/2002 | Torchia et al. ............... 600/411 |
| 6,516,211 B1 | | 2/2003 | Acker et al. |
| 6,522,142 B1 | * | 2/2003 | Freundlich ................... 324/315 |
| 6,542,767 B1 | * | 4/2003 | McNichols et al. .......... 600/407 |
| 6,582,381 B1 | * | 6/2003 | Yehezkeli et al. ................ 601/2 |
| 6,618,620 B1 | * | 9/2003 | Freundlich et al. ............ 607/27 |
| 6,671,535 B1 | * | 12/2003 | McNichols et al. .......... 600/407 |
| 6,676,654 B1 | | 1/2004 | Balle-Petersen et al. |
| 6,735,461 B2 | * | 5/2004 | Vitek et al. ................... 600/411 |
| 6,773,408 B1 | * | 8/2004 | Acker et al. ...................... 601/2 |
| 7,759,937 B2 | * | 7/2010 | He et al. ....................... 324/318 |
| 7,771,418 B2 | * | 8/2010 | Chopra et al. .................. 606/28 |
| 8,175,676 B2 | * | 5/2012 | Chang .................... A61B 5/416 |
| | | | 600/411 |
| 8,224,420 B2 | * | 7/2012 | Mu et al. ...................... 600/411 |
| 8,231,557 B2 | | 7/2012 | Moonen et al. |
| RE43,901 E | * | 1/2013 | Freundlich et al. ............ 606/27 |
| 2004/0249261 A1 | * | 12/2004 | Torchia et al. ............... 600/411 |
| 2008/0194941 A1 | * | 8/2008 | Steinmeyer et al. .......... 600/411 |
| 2008/0275330 A1 | * | 11/2008 | Mu et al. ...................... 600/411 |
| 2010/0280356 A1 | | 11/2010 | Kohler et al. |
| 2011/0152730 A1 | * | 6/2011 | Kohler ...................... A61N 7/02 |
| | | | 601/3 |
| 2011/0313329 A1 | * | 12/2011 | Kohler ...................... A61N 7/02 |
| | | | 601/3 |
| 2011/0319747 A1 | * | 12/2011 | Schmidt et al. ............... 600/411 |
| 2012/0083686 A1 | * | 4/2012 | Virta et al. .................... 600/411 |

FOREIGN PATENT DOCUMENTS

| | | |
|---|---|---|
| JP | 2004344672 | 12/2004 |
| WO | WO0135825 | 5/2001 |
| WO | WO0166189 | 9/2001 |
| WO | WO02085457 | 10/2002 |
| WO | WO2005107869 | 11/2005 |

OTHER PUBLICATIONS

R. Gunduz, "A Homework for Magnetic Resonance Guided Focused Ultrasound Surgery (MRgFUS)", submitted to Istanbul Technical University at Istanbul, May 13, 2005, pp. 1-14.

R. Salomir, et al., "Local Hyperthermia With MR-Guided Focused Ultrasound: Spiral Trajectory of the Focal Point Optimized for Temperature Uniformity in the Target Region", Journal of Magnetic Resonance Imaging vol. 12, No. 4, Oct. 2000, pp. 571-522.

* cited by examiner

THERAPY SYSTEM WITH TEMPERATURE CONTROL

CROSS REFERENCE TO RELATED CASES

Applicants claim the benefit of International Application Number PCT/IB2009/050080, filed Jan. 9, 2009, and Provisional Application Ser. No. 61/020,782, filed Jan. 14, 2008.

FIELD OF THE INVENTION

The invention pertains to a therapy system which comprises a therapy module to perform a therapeutic action along a trajectory through a target zone. The therapy system also comprises a thermometry module to measure temperature of a measurement field and a control unit to control the therapy module on the basis of the measured temperature.

BACKGROUND OF THE INVENTION

Such a therapy system is known from the paper 'Local hyperthermia with MR-guided focused ultrasound: spiral trajectory for the focal point optimized for temperature uniformity in the target region' by R. Salomir et al. in J. Magn. Res. Im. 12(2000)571-583. This paper discloses a therapy system which is an MR-guided focused ultrasound system. The therapy module is formed by a spherical ultrasound transducer of which the focus is moved along a double inside-out spiral trajectory covering the target region. The intensity of the acoustic field of the spherical ultrasound transducer has approximately a Gaussian distribution around the focal point. A magnetic resonance imaging system provides both anatomical information for target definition and temperature maps. The cited paper mentions to employ fast MR-thermometry and on-line feedback to the ultrasound apparatus. A feedback algorithm is based on real-time evaluation of temperature gradients around the focal point. In particular, the focal spot is moved over the spiral trajectory under continuous and maximum focused ultrasound power. Differences between the real and a target temperature during the first spiral are corrected during the second spectral trajectory.

SUMMARY OF THE INVENTION

An object of the invention is to provide a therapy system that is more reliable and has a higher accuracy in applying the therapeutic action.

This object is achieved by a therapy system of the invention which comprises
 a therapy module to direct a therapeutic action to a target along successive trajectories in a target region that includes the target
 a thermometry module to measure temperature a measurement field and in particular to compute a thermal dose,
 a control module to control the therapy module to apply the therapeutic action along the respective trajectories on the basis of the measured temperature and/or thermal dose, wherein
 the successive trajectories are located in the target zone outward or inward relative to one another within the target zone.

The therapeutic action, notably the deposition of energy in the target zone is directed along pre-determined subsequent trajectories. When the therapeutic action is performed along one of the trajectories, then the trajectory itself as well as an area or volume around the trajectory are affected by the therapeutic action. Diffusion of the therapeutic action causes that a zone around the trajectory is affected. This is notably the case when energy is deposited at the trajectory and thermal diffusion causes the zone around the trajectory to be heated. According to the invention the temperature of the measurement field is measured. The temperature of the measurement field is representative for the temperature of the target zone. Often it is sufficient that the measurement field is located within the target zone. More accurate results are obtained when the measurement field covers the entire target zone. On the basis of the measurement at a current application of the therapeutic action i.e. deposition of energy along a current trajectory, it is determined whether to apply the therapeutic action along a subsequent trajectory. In the outward case, successive trajectories are located outward relative to one another and relative to the target or inward starting at periphery of the target zone. The current trajectory encloses the trajectory along which previously the therapeutic action has been performed. Thus, as the therapeutic action is applied along subsequent trajectories, the therapeutic action is applied to the target zone as the diffusion of deposited heat progresses outwardly over the target zone. In the inward case, the subsequent trajectory moves towards the centre of the target zone. Because the application of the therapeutic action along a next located trajectory is dependent on the measured temperature, a forced diffusion pattern is generated. This forced diffusion pattern accurately generates the temperature distribution that has the intended therapeutic effect. This enables to achieve a rather even temperature at the completion of energy deposition at respective trajectories. The control of the therapy module on a trajectory-by-trajectory basis does not require to control the power level of the therapy module, but only the time whether and/or when to switch to the next trajectory. This provides a binary and therefore very robust and simple feedback control for the therapy module. In particular along individual trajectories the power level can be kept at maximum, producing necrosis faster and thus resulting in a more efficient treatment. When the power level is kept at exceeding a level to cause necrosis of the tissue, notably when the power level is kept at maximum, then necrosis is caused along and around each previous trajectory. Should energy deposition be interrupted for some reason, then necrosis is already caused in the portion of the target zone covered by the previous trajectories. Thus, when energy deposition is resumed, then there is no need to resume for the whole target zone, but energy deposition can be resumed at the trajectory in which the interruption took place.

The trajectories can be two-dimensional and cover a target zone that is an area. The trajectories can be three-dimensional and enclose a volume target zone. If target region is of extremely oblong shape, such as a thick line or a pencil shaped region, then one-dimensional trajectories can potentially be advantageous, although only one trajectory would be possible and the utilization of thermal energy build-up will only be along the line.

These and other aspects of the invention will be further elaborated with reference to the embodiments defined in the dependent Claims.

In another aspect of the invention the deposition of energy along a next trajectory is decided on the basis of whether the current thermal dose exceeds a predetermined limit. In this way the deposition of energy can accurately follow the diffusion of heat due as energy is deposited. When the deposition of energy along a next trajectory is based on both the measured temperature and the applied thermal dose a rather even temperature in the target zone is achieved in such a manner that necrosis is caused in the tissue in the target zone.

In particular, the measured temperature and the thermal dose used as decision criteria may be different for individual trajectories. Having a higher temperature limit than strictly needed in the inner trajectories as compared to the outer trajectories, will cause an extra thermal build-up at the inner trajectories that diffuses onto the outer trajectories with time. This reduces the necessary energy needed at the outer trajectories (since applying thermal energy gives a higher temperature build-up in the inner trajectories due to less diffusion out of treatment area) and shortens the total treatment time, making treatment far more efficient. Further, the decision to deposit energy along a next trajectory may be based on measured temperature only for some current trajectories. For other current trajectories the decision may be based on the combination of measured temperature and thermal dose. The measured temperature and thermal dose are not independent, but dose predicts necrosis (the ultimate goal of the treatment) whereas temperature control ensures 1) reaching of dose (temperatures at or above some 54-56 degrees create dose of 240EM within a few seconds) and 2) an efficient treatment if higher temperature limits are used in the inner trajectories. Dose control itself can be used to control the therapeutic action but exponential and integral relationship on temperature makes less practical to implement. Especially, the decision to deposit energy along a final trajectory of a set is to be based on both measured temperature and thermal dose. In this way necrosis is caused in the target zone within the final trajectory, while a lethal dose outside the final trajectory is avoided. Thus, effective treatment is achieved while healthy tissue at the periphery of the target zone is spared. Optimal target values for the temperature and thermal dose to achieve necrosis in tissue can be achieved by using simulations. For example, good results have been obtained on the basis of the Pennes' bioheat equation relating temperature change to thermal diffusion, power absorption and perfusion. The decision to apply energy deposition along a next trajectory may be based on an analysis of temperature and/or thermal dose along the voxels of the current trajectory or in a measurement field within the images or by examining all acquired temperature images. The first implementation, analysing the temperature or dose along the current trajectory, involves a relatively low computational effort. Alternatively, the decision to apply energy deposition along a next trajectory may be based on an analysis of temperature and/or thermal dose along the voxels of the preceding and/or the current trajectory and/or a larger measurement field. This implementation involves a larger computational load, but is more accurate and more robust. The temperature and/or thermal dose can be evaluated on the basis of statistical quantities derived from the values for individual voxels or pixels. Particularly good results are obtained for the accurate decision to deposit energy along a next trajectory on the basis of mean, minimum or median temperature of the voxels within and/or of the current trajectory. Further, e.g. standard deviation can be used to determine goodness of data and if it exceeds a limit then treatment can be stopped before dangerous outside of treatment zone treatment occurs due to e.g. muscle spasms, tension or similar.

In a further aspect of the invention the trajectories have equal or similar shape. This is easy to implement. Moreover, equally or similarly shaped and outwardly located relative to one another cause heat diffusion due to energy deposition along previous inner trajectories to be evenly distributed. Very good results are achieved for concentric trajectories. Smooth or regularly shaped trajectories achieve uniform heat diffusion because diffusion from point-source is spherical (in a volume) or circular (in a plane), in homogeneous media. When the trajectories have corners, heating at the corners is less efficient. More power must be deposited at these corners than elsewhere for even heating to occur. Ideally, smooth trajectories such a circles of spheres on the other hand are more difficult to steer the therapeutic action, deposition of energy, along. A good compromise for mechanically performed trajectories is formed by hexagonal trajectories along which it easy to control the deposition of energy, while the number of corners remains small. For electronically moved trajectory, circles are the best choice due heat-diffusion being spherical or circular in homogeneous media.

In another aspect of the invention the duration of the therapeutic action is set to a pre-set maximum duration. The value of the maximum duration may be dependent on the individual trajectory. In this way continuation of the therapeutic action longer than what is acceptable is prevented.

In another aspect of the invention the energy levels within individual trajectories may be varied to provide uniform heating. For example, local perfusion or may cause one section of a trajectory to heat less than other sections of the trajectory. The thermal module will show this variation. In these cases where trajectories are large enough to have non-uniform heating, the trajectory can be broken into sub-trajectories. For example, with the concentric circle trajectories, sub-trajectories may be arcs. The movement between sub-trajectories can the be controlled in a similar manner as movement between trajectories. Such an approach will compensate for non-uniform heating profiles that many occur in large trajectories due to local diffusion or perfusion effects.

In a particular example of the invention the therapy unit is a high-intensity focused ultrasound system. In this example the deposition of energy is performed by the high-intensity ultrasound waves; this technique is termed 'sonication'. The therapeutic action, notably sonication, can be performed along one-dimensional intervals, along trajectories that cover a two-dimensional area or fill a three-dimensional volume. Other examples of the therapy unit are a microwave applicator or a cryotherapy system.

In another example of the invention the thermometry module is implemented in a magnetic resonance examination system. In this example the temperature is derived from the magnetic resonance signals generated in the target zone. The temperature in the target zone can be derived from the phase of the magnetic resonance signals. To this end, in moving tissue, accurate motion correction is carried out to separate phase contribution due to temperature and motion, respectively.

The invention also pertains to a method to direct the therapeutic action to the target zone in which the therapeutic action is directed toa target along subsequent trajectories in a target region that includes the target, by a method comprising: measuring temperature in a measurement field, controlling the application of the therapeutic action along respective trajectories on the basis of the measured temperature, wherein subsequent trajectories are located in the target zone outward or inward relative to one another from the target. The method of the invention includes controlling the therapy system of the invention, notably to control the therapy module on the basis of the measured temperature to apply the therapeutic action along subsequent trajectories in the target zone.

The invention further relates to a computer programme defined as comprising instructions to direct a therapeutic action to a target along subsequent trajectories in a target region that includes the target, measure temperature in the measurement field, control the therapy module to apply the therapeutic action along respective trajectories on the basis of the measured temperature, wherein subsequent trajectories are located in the target zone outward or inward relative to one another from the target. The computer programme of the invention can be provided on a data carrier such as a CD-rom disk or a USB memory stick, or the computer programme of the invention can be downloaded from a data network such as the world-wide web. When installed in the computer included in a therapy system the therapy system is enabled to operate according to the invention and achieve accurate therapeutic action, notably deposition of energy and causing necrosis in the target zone.

BRIEF DESCRIPTION OF THE DRAWINGS

These and other aspects of the invention will be elucidated with reference to the embodiments described hereinafter and with reference to the accompanying drawing wherein.

DETAILED DESCRIPTION OF THE PREFERRED EMBODIMENTS

Figure 1:
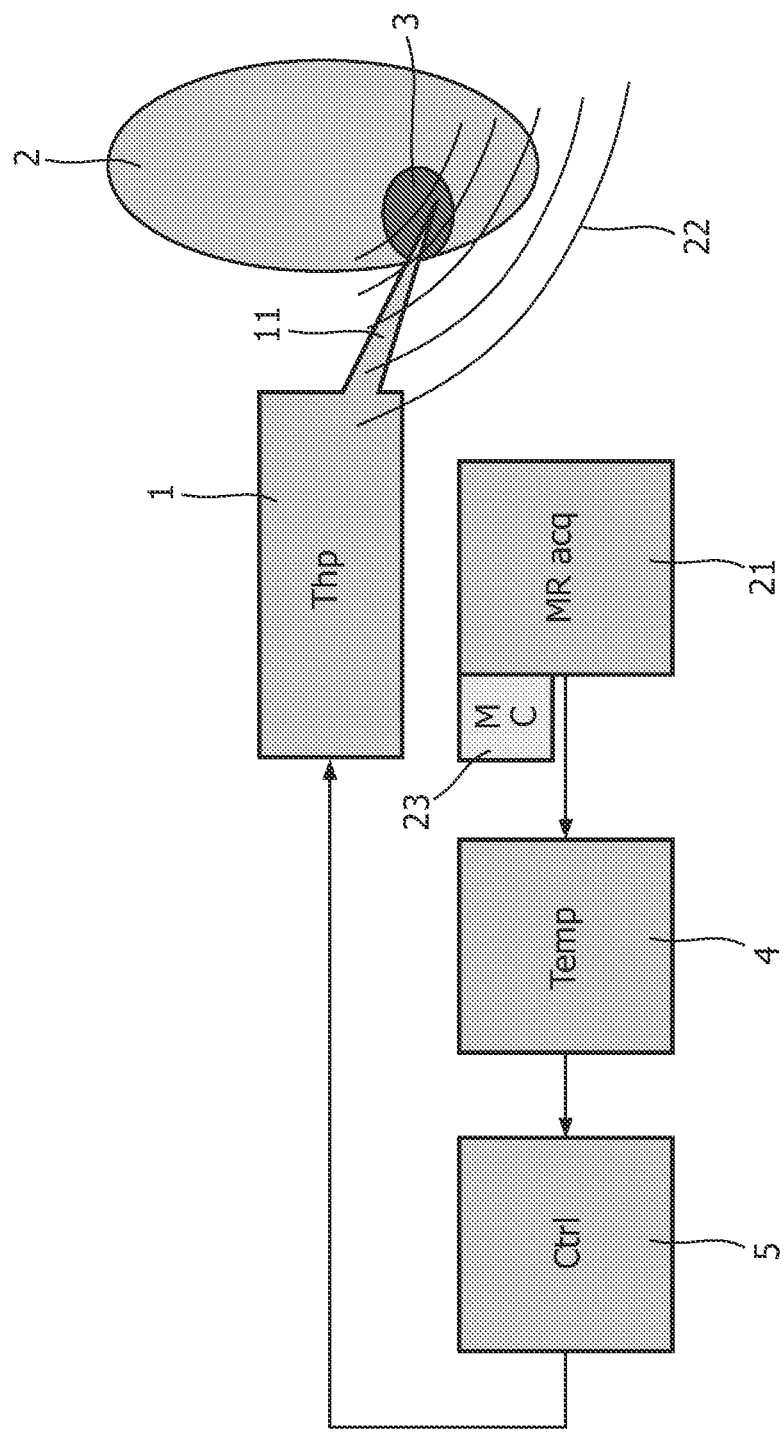
FIG. 1 shows a diagrammatic representation of the therapy system in which the invention is employed.

FIG. 1 shows a diagrammatic representation of the therapy system in which the invention is employed. The therapy unit 1, for example in the form of a high-intensity focused ultrasound (HIFU) unit generates a therapeutic action in the form of a focused ultrasound beam 11. The focused ultrasound beam 11 is accurately directed onto a target zone 2 that includes the actual target 3. For example the target is a tumour in (part of) an organ 2 of the patient to be treated. The HIFU unit 1 is operated so that the focused ultrasound beam 11 moves over subsequent trajectories (see FIG. 2 for examples) in the volume of the target zone 2. The ultrasound beam 11 deposits energy along these trajectories, causing elevated temperature along the trajectories. In this way the tissue within individual trajectories is raised to a level where necrosis of the tissue occurs. Ultimately necrosis occurs in the tissue of the tumour and around it in the target zone once the desired thermal dose or temperature is reached. In particular the thermal dose can be calculated in a simple approximation as $$TD = \int_0^t r^{43-T(\tau)} d\tau,$$

where $r = 0.25$ when $T < 43° C.$ and $r = 0.5$ when $T >= 43° C.$

A dose limit of 240 equivalent minutes at 43° C. is typically thought to result in necrosis. A modified version of the equation exists that takes effect of uncertainty into account. In this scope one or several limits (or potentially a lower one) can be checked to ensure that once reached, therapy is stopped or trajectory switched. Following temperature only, tells us that necrosis will most probably occur, whereas thermal dose ensures us of it.

For example, necrosis is achieved when the intensity of at the focus of the focused ultrasound beam is about 1600 Wcm$^{-2}$. At this maximum energy level efficient necrosis is achieved without the risk of cavitation. The ultrasound beam can also be used to elevate tissue temperatures to non-necrosis temperature levels. These lower temperature are useful in hyperthermia type applications.

The temperature distribution of the measurement field is derived from magnetic resonance signals. To this end the patient is placed in an magnetic resonance examination system (not shown) and magnetic resonance signals 22 are generated. The magnetic resonance signals are received by the MR signal acquisition system 21 that is part of the magnetic resonance examination system. The MR signal acquisition system includes RF receiving antennae (coils) and a signal processing system, such as a spectrometer. The acquired magnetic resonance signals are applied to the thermometry module 4 which derives the temperature distribution in the target zone. The phase of the magnetic resonance signals depends on temperature. The magnetic resonance signals are spatially encoded by means of encoding magnetic gradient fields, such as read and phase encoding gradients. The spatial resolution of the magnetic resonance signals and the ensuing temperature distribution is at the scale of a millimetre; even sub-millimetre resolution can be obtained where the smallest detail that can de distinguished has a size of a few tenths of a millimetre.

For example if there are several slices in the stack monitoring the temperature, then the measurement field used for deciding whether to switch trajectory or not can advantageously be projected to all parallel slices in the focal-region even though the focal-point trajectory is only in the middle slice of the stack. Because the widest and hottest plane of the typically ellipsoidal heated region may wander towards the transducer during heating, this reduces the risk of the treated region having a larger radius than desired measured from the beam-axis. A measurement field along the beam-axis can also be applied to control that the 240EM dose length does not exceed a maximum length if we have a sagittal plane (which we do). This improves safety considerably. Hence, sonication trajectory and area looked at for decision criteria (measurement fields) are separated.

Accurate results in moving tissue are obtained when a motion correction is applied and phase contribution due to motion are separated from phase contributions due to temperature changes. The motion correction can be derived from the magnetic resonance signals, notably by redundant magnetic resonance signals from the central portion of k-space. To this end acquisition strategies that oversample the centre of k-space are suitable, such as radial, spiral or PROPELLER acquisitions. Also MR navigator signals are particularly useful to derive motion and only require a short acquisition time. A motion compensation module 23 is provided to derive the motion correction and apply motion compensation to the magnetic resonance signals. The motion corrected magnetic resonance signals are applied to the thermometry module 4 which derives local temperature distribution of the target zone 3. Alternatively, the motion compensation module 23 can be configured or programmed in software to derive separate the contribution to the phase of magnetic resonance signals due to motion and compute the contribution of the phase due to temperature changes. The local temperature distribution is applied to the control module 5, which controls the therapy module, i.e. the HIFU unit 1 to focus the focused ultrasound beam along a next trajectory. The centre of concentricity can for example be continuously evaluated (e.g. by Gaussian fits or weighted average) to take into account the possibility of the treated (notably heated) region shifting slightly (typically 1-2voxels or 0.5-5 mm) during treatment due to e.g. spasms or slightly non-uniform heat diffusion.

Figure 2:
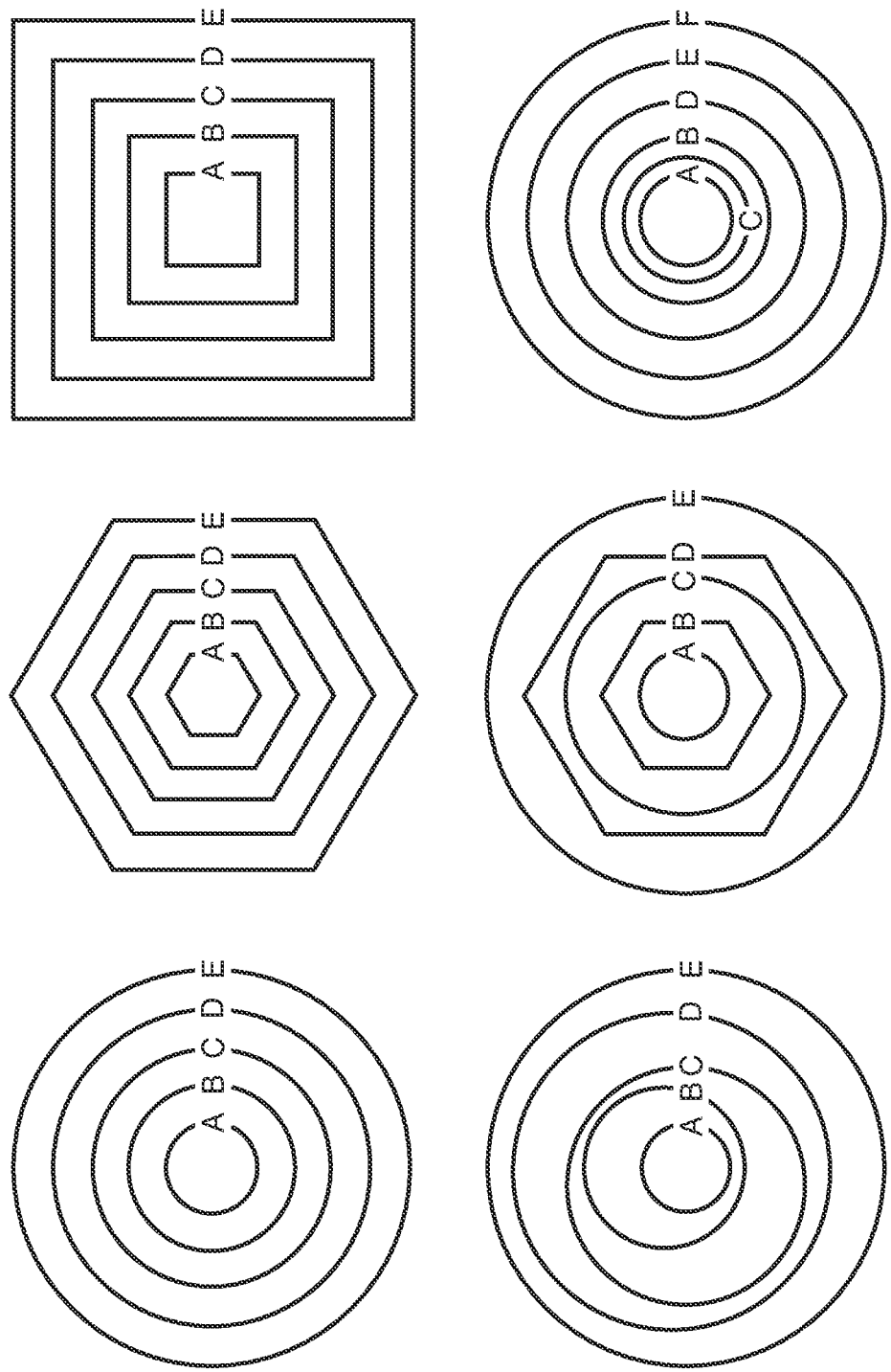
FIG. 2 shows various examples of sets of subsequent trajectories along which the therapeutic action is applied according to the invention.

FIG. 2 shows various examples of sets of subsequent trajectories along which the therapeutic action is applied according to the invention. In an individual example the succession of trajectories along which the focused ultrasound beam is focussed in indicated alphabetically A,B, . . . E. Examples are in particular concentric circles, concentric hexagons or concentric squares. These examples are easy to implement and the concentric circles, for mechanical motion hexagons, are particularly efficient is depositing energy uniformly and yet requires relatively simple control. More intricate example, such as non-concentric circles, a mixture or various concentric different shapes or concentric circles at non-uniform mutual distance are effective in achieving a more accurate but effective deposition of energy to achieve required temperature and/or thermal dose over the target zone.

The invention claimed is:

1. A therapy system comprising:
a therapy module directing a therapeutic action to a target along a first trajectory and along successive trajectories in a target zone that includes the target, wherein the first trajectory and the successive trajectories are concentric and comprise closed geometric shapes,
a thermometry module measuring temperature in a measurement field and computing a thermal dose applied by the therapy module, the measurement field at least partially covering the target zone, and
a control module controlling the therapy module to direct the therapeutic action from the first trajectory to a one of the successive trajectories on the basis of at least one of the measured temperature and the computed thermal dose, wherein
the first trajectory and the successive trajectories are located entirely inside of or entirely outside of one another within the target zone.

2. A therapy system as claimed in claim 1, wherein
the control module directs the therapy module to apply the therapeutic action along one of the successive trajectories
on the basis of the measured temperature and the computed thermal dose exceeding respective predetermined threshold values,
the respective pre-determined threshold values being dependent on respective associated trajectories.

3. A therapy system as claimed in claim 1, wherein the thermometry module computes an applied thermal dose to the target zone from the measured temperature.

4. A therapy system as claimed in claim 1, wherein the control module controls the duration of the therapeutic action to not exceed a preset maximum duration.

5. A therapy system as claimed in claim 1, in which the therapy module is a high-intensity focused ultrasound system.

6. A therapy system as claimed in claim 1, in which the thermometry module is a magnetic resonance examination system which is arranged to derive the temperature of the target zone from magnetic resonance signals.

7. A therapy system as claimed in claim 1, in which the first trajectory or the one of the successive trajectories is broken into sub-trajectories that are transitioned on the basis of at least one of the measured temperature and the computed thermal dose to compensate for non-uniform energy deposition within the respective first trajectory or the one of the successive trajectories.

8. A method for applying a therapeutic action to a target, comprising:
directing a therapeutic action to a target along a first trajectory in a target zone that includes the target,
measuring temperature in a measurement field, the measurement field at least partially covering the target zone, and
directing application of the therapeutic action to a successive trajectory in the target zone that includes the target on the basis of the measured temperature,
wherein the first trajectory and the successive trajectory are concentric and comprise closed geometric shapes,
wherein the first trajectory and the successive trajectory are located entirely inside of or entirely outside of one another within the target zone.

9. A computer program product comprising a non-transitory computer readable storage device having encoded thereon instructions which when executed by a processor cause:
a therapy module to direct a therapeutic action to a target along a first trajectory and successive trajectories in a target zone that includes the target, wherein the first trajectory and the successive trajectories are concentric and comprise closed geometric shapes,
a thermometry module to measure temperature in a measurement field, the measurement field at least partially covering the target zone,
a control module to direct application of the therapeutic action to one of the successive trajectories on the basis of the measured temperature, wherein
the first trajectory and the successive trajectories are located entirely inside of or entirely outside of one another within the target zone.

* * * * *